US005506408A

United States Patent [19]
Vickers et al.

[11] Patent Number: 5,506,408
[45] Date of Patent: Apr. 9, 1996

[54] GAMMA CAMERA

[75] Inventors: David S. Vickers, Independence; Geoffrey G. Cochrane, Chippewa Lake, both of Ohio

[73] Assignee: Summit World Trade Corporation, Hudson, Ohio

[21] Appl. No.: 218,361

[22] Filed: Mar. 28, 1994

Related U.S. Application Data

[63] Continuation-in-part of Ser. No. 922,695, Jul. 30, 1992, abandoned.

[51] Int. Cl.⁶ ..................................................... G01T 1/20
[52] U.S. Cl. ........................................... 250/366; 250/367
[58] Field of Search ...................................... 250/366, 367

[56] References Cited

U.S. PATENT DOCUMENTS

4,942,302  7/1990  Koechner .................................. 250/368
5,103,098  4/1992  Fenyves .................................... 250/368
5,175,434  12/1992  Engdahl .................................... 250/366

Primary Examiner—Constantine Hannaher
Attorney, Agent, or Firm—Watts, Hoffmann, Fisher & Heinke C.

[57] ABSTRACT

A gamma camera having separate detectors respectively to determine the spatial location and energy of gamma radiation emanating from a patient is disclosed. The preferred camera has two adjacent, mutually perpendicular arrays of parallel, coordinant signal producing scintillaters positioned on the face of a scintillating energy crystal. Each of the fibers within the arrays conducts light resulting from Compton events to an associated one of a set of photodetectors to produce coordinant signals. Other photodetectors monitor the total scintillated energy within the energy crystal. The energy crystal is of sufficient size to absorb energy remaining in each patient emitted gamma ray that has produced Compton events in the coordinant scintillators. The sum of the energies of substantially coincident signals from the fibers and the crystal is used to identify photo peak events.

34 Claims, 4 Drawing Sheets

GAMMA CAMERA

CROSS REFERENCE TO RELATED APPLICATION

The present application is a continuation-in-part of application Ser. No. 07/922,695 filed Jul. 30, 1992, entitled "Gamma Camera" to Vickers et al, now abandoned.

FIELD OF THE INVENTION

This invention pertains to gamma imaging devices and more particularly to that class of devices known as scintillation cameras.

BACKGROUND ART

In the diagnosis of certain illnesses, radioactive agents are administered to patients. These administered agents have the characteristic of localizing in certain tissues and either not localizing, or localizing to a lesser degree, in other tissues. For example, iodine 131 will localize in thyroid glands. A representation of the spatial distribution and concentration of administered iodine 131 in a thyroid gland provides an image of the gland itself which is useful in diagnosing the condition of the gland.

In many studies, devices known as cameras which remain stationary with respect to the patient produce a representation of the spatial distribution of radioactivity. With commercially successful cameras, known as Anger-type cameras, a relatively large disc-shaped scintillation crystal is positioned to be stimulated by radiation emitted from the patient. A collimator is interposed between the patient and the crystal so that, for example, with a parallel hole collimator the rays striking the crystal are all generally perpendicular to it.

When incident radiation collides with a scintillation detector or crystal, the collision excites an electron into a higher energy state. When the electron drops back into its ground state, photons are emitted within a visible spectrum and can be observed by appropriately positioned photodetectors.

The conversion of energy from the radiation into light energy can occur in different ways. In a so-called photoelectric recoil occurrence, the entire energy of the gamma ray is used to excite a bound electron which then decays providing a photon. When this occurs, the gamma radiation is totally dissipated into the creation of the photon.

A second possibility is that the gamma radiation can produce visible light radiation by means of a Compton event. The gamma radiation interacts with a free electron, but rather than giving up all its energy to the electron which later is converted to light, only a portion of the energy is transmitted to the electron. This results in a scattering of the gamma radiation and produces visible light at the same time. The scattered gamma radiation can move a further distance through the scintillation crystal and later cause other photon-producing events including a photo-electric recoil of the remaining energy. With an Anger-type camera, photopeak events which are either both single photo-electric recoils and sequential events are used to produce images.

A third event that can produce visible light within the scintillation crystal is energy conversion of the gamma radiation into a positron-electron pair. The positron quickly recombines with an additional free electron in the crystal in a positron-electron annihilation. When the positron and electron annihilate each other, two gamma rays of energy 511 keV each are produced which then interact in one of the previously described ways. Typically, positron radiation is not used with Anger-type cameras.

When the crystal of an Anger-type camera scintillates, light is conducted through a suitable light pipe, to an array of phototubes. When a phototube is stimulated by gamma-generated light from a crystal, an electrical signal is emitted which is proportional to the intensity of light energy received by that tube. When a scintillation causes all or substantially all of the phototubes to emit signals, these signals are emitted concurrently and are then summed to provide a signal known as the Z signal used for energy resolution. For energy resolution, this Z signal is conducted to a pulse-height analyzer to determine whether the energy of the signal reflects the occurrence of a photopeak event caused by the isotope which has been administered to the patient. That is, the Z signal is of appropriate strength to reflect the full conversion of the energy of a gamma ray emitted from the administered isotope to light energy by the crystal.

Summing and ratio circuits are also provided which develop coordinate signals known as X and Y signals. These X and Y signals cause a dot to be produced on the screen of the oscilloscope at a location spatially corresponding to the location of the detected scintillation. Thus, the oscilloscope dots are displaced relatively, each at a location corresponding to the location of the corresponding scintillation in the crystal. The oscilloscope dots are integrated to produce an image.

The phototubes, the circuits and the oscilloscope function as a unit to provide a light amplifier such that each dot produced on the oscilloscope is a brightened representation of a scintillation. Through the use of persistence screen on the scope, or a photographic camera, dots produced in a study have been integrated to produce images.

With Anger-type cameras and other proposals which would, like the typical Anger camera, produce a plan view of a region under investigation, a photoelectric recoil has been considered to be an ideal event. That is, an event in which the entire energy of an incident gamma ray is converted to a light or an electrical output signal in a single interaction with a crystal or other transducer. A photoelectric recoil is desired because there is a single locus for spatial resolution. Since many of the output signals of a camera result from photopeak events which are in fact produced by a series of interactions, there is an inherent systemic limitation on the spatial resolution capabilities of a camera. The limitation results from the fact that loci of the interactions are spaced and resulting coordinate signals provide a "composite" locus offset from the true incident gamma ray path.

In order to minimize the inherent spatial error in an Anger-type camera, manufacturers have resorted to the use of very thin crystals. While the use of thin crystals enhances the spatial resolution of a camera, it reduces the efficiency of the camera because rays more readily pass through the crystal without full energy conversion to produce a photopeak event. It also precludes the use of certain higher energy isotopes such as 511 keV positron radiation because too low a percentage of the high energy rays result in photopeak events. In addition, the thin crystals are relatively weak and excessively susceptible to breakage which destroys their imaging usefulness.

A common systemic limitation of the capabilities of both Anger cameras and other prior proposals for gamma cameras is that each set of coordinate signals for spatial resolution and the associated Z signal for energy resolution derive from the same event. Since one event is used for both spatial and energy resolution, there is a consequent sacrifice of one or both of spatial resolution accuracy and camera efficiency.

With an Anger-type camera, the need for a collimator in all types of studies further limits the camera efficiency. A parallel hole collimator only passes of the order of ten percent of the patient-emitted energy to the crystal while a pinhole-type collimator is even less efficient.

SUMMARY OF THE INVENTION

With a camera made in accordance with the present invention, sequential and separate events are used separately to establish first spatial, and then energy resolution. To accomplish this, a spatial resolving mechanism is interposed between the subject under investigation and a thick gamma-converting layer. Coordinate spacial resolutions signals are derived only from events occurring in the spacial mechanism. Outputs of the spatial resolving mechanism and the thick layer are summed to produce a Z signal. Since separate events are used, cameras embodying this invention, operate on a principle diametrically opposed to prior cameras. The principle is different because a single photo-electric recoil not only is not preferred but, with but a rare exception in one embodiment, will not contribute to a camera-produced image. The enhanced efficiency is produced because the thick gamma converting or energy layer, since it does not contribute to spacial resolution, can be of sufficient mass to assure energy conversion of a very high percentage of incident radiation.

The one exception is in that embodiment where a single member is used to produce both coordinate signals and a single photo-electric recoil event occurs in that member, the photo-electric recoil will contribute to a resulting image. Such an occurrence is extremely rare, if indeed, it ever occurs at all.

Through use of separately established spacial and energy signals, the present cameras provide enhanced efficiency through development of a significantly higher percentage of image-producing signals from incident gamma rays than prior actual and proposed cameras produced.

The enhanced efficiency is produced because the thick gamma converting or energy layer, since it does not contribute to spacial resolution, can be of sufficient mass to assure energy conversion at a very high percentage of incident radiation. In addition, studies with positron energy of 511 keV, which are typically not conducted with present day commercially available cameras, can be performed because the thick energy crystal will convert even such high energy radiation into photopeak events.

Apparatus constructed in accordance with one embodiment of the invention is used in diagnosing a condition of a patient by monitoring gamma radiation emanating from the patient. A spatial detection member converts incident penetrating radiation to an electronic signal. The spatial detection member has a thickness to provide a high probability of a signal-producing event from a Compton-type interaction as radiation moves through the member. Where the spacial detection member is a light emitter, detectors for converting the event into electronic signals are positioned next to the detection member. Outputs from the detectors are used to determine a co-ordinate position of a detected event. After gamma radiation has passed through the spatial detection member, it interacts with an energy detection member. The energy detection member absorbs essentially all of the remaining energy of each incident ray and produces a final signal event. When the energy detection member is a light emitter, detectors for converting each final signal event to electronic signals are positioned next to the energy detection member. Outputs from these detectors are summed with the total output from the spatial detection member to produce a signal used to determine the energy of the penetrating radiation.

According to another embodiment, the spatial detection member consists of two mutually perpendicular arrays of parallel scintillation fibres positioned near a thick body of scintillation material, typically a scintillation crystal such as thallium activated sodium iodide. A photodetector is provided at the end of each fibre, while another array of photodetectors is provided to monitor the energies of light-producing events in the thick body. The parallel fibres within each array provide output signals in a planar coordinate system to establish the locus of each detected incident ray. The total energy of light-producing events in the thick body and the arrays occurring within a pre-selected time period is used to identify desired photopeak energy conversion and to exclude readings produced by radiation scattered within the patient or generated by an extraneous source. The positions of readings which are not excluded are integrated to produce an image of the subject.

In this embodiment, the energy detection member preferably consists of a crystal, prismatic and preferably a rectangular solid in shape, of thallium-activated sodium iodide, 50 mm thick. The output of this crystal is concentrated by light pipes or other optical coupling to one or more photodetectors. Light for these photodetectors may be extracted from the sides or from the rear surface of the scintillating material.

For the dimensional studies using one or more detectors to orbit the patient and back projection to produce an image, with a detector made in accordance with the invention, the need for a collimator is eliminated. More specifically, by adding additional spatial detection member(s), it is possible to determine the direction of each incoming gamma photon. Each spatial detection member will provide an x and y coordinate while the positions of the spatial detection members themselves provide a z coordinate. It is a well known principle in mathematics that two points uniquely determine a line, so, within the resolution limits of the spatial detection members one can determine along what line the gamma photon travelled. By removing any collimating device from between the spatial detectors and the patient, gamma photons from all directions will be detected allowing a much higher count rate while still providing for excellent resolution within the patient. Indeed, the resolution will be:

$$R = (1 + (2*OCD)/d)*fd$$

where:

R is the resolution in mm

OCD is the patient (object) to camera face distance in mm d is the separation between spatial detection members in mm fd is the resolution in the spatial detection member in mm As can be seen from the above equation, as the separation distance between the two spatial detection members increases, the resolution in the patient approaches the resolution in the spatial detection members themselves.

BEST MODE FOR PRACTICING THE INVENTION

Figure 1:
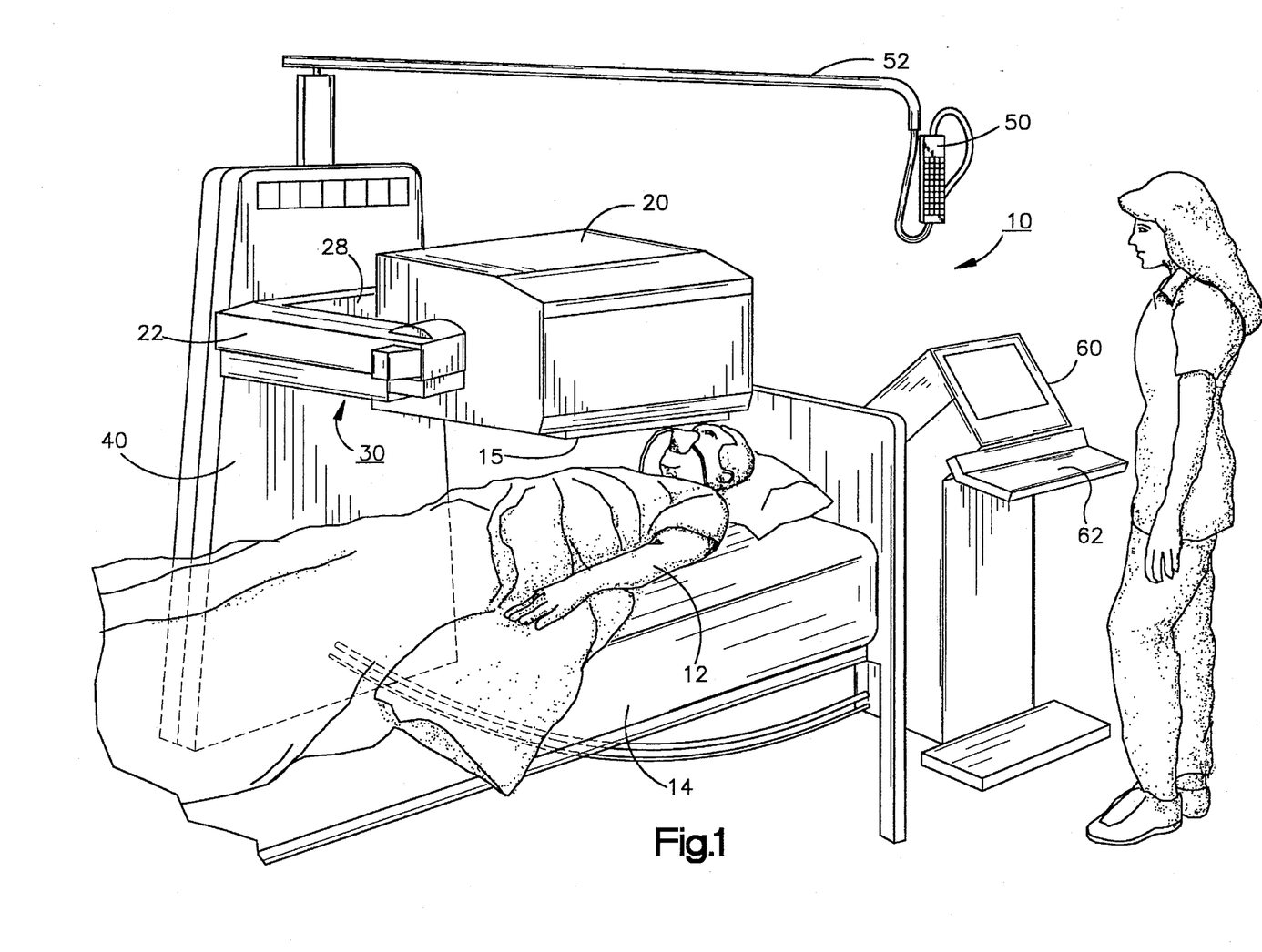
FIG. 1 is a schematic depiction of a gamma camera diagnostic system.

Turning now to the drawings, FIG. 1 is a schematic depiction of a gamma camera system 10 for imaging the internal structure of a patient 12 positioned on a horizontal support 14. Typically, the gamma camera system 10 monitors a radioactive agent which is administered to the patient 12 and accumulates in a specific region of interest. As the radioactive agent emits gamma radiation, the radiation exits the patient, passes through a collimator 15, FIG. 1 and is monitored to allow an image of the region of interest to be generated. The position in the patient from which each photon of gamma radiation is emitted is determined in an x-y coordinate system, and an image depicting the density of radiation emanating from different points within the patient is generated from an integration of the position readings.

The gamma camera system 10 includes a scintillation crystal system mounted behind a beam collimator 15 and inside a detector housing 20. The housing 20 is pivotally mounted on a gantry having two arms 22 (only one of which is seen in FIG. 1) that support the detector housing. The arms 22 are joined together by means of a cross piece 28 to form a generally C-shaped yoke 30 within which the detector housing 20 pivots. The yoke 30 is in turn pivotally connected to an upright stanchion 40 that can be re-positioned within a hospital room. The stanchion 40 is supported by rollers (not shown) that allow the stanchion to be rolled next to a patient support.

A control unit 50 coupled to the stanchion by means of an overhead arm 52 includes push button controls that allow an operator to re-orient the yoke 30 and detector housing 20 after the stanchion and patient have been positioned next to one another. Electric motors inside the stanchion accomplish this reorienting.

The horizontal support 14 depicted in FIG. 1 is a hospital bed. Alternately, the horizontal support 14 might include a specially constructed support in which the patient or patient is positioned during imaging. Such a support would include means for moving the patient relative to the gamma camera housing.

Gamma camera images are presented on a viewing console 60 having a control keyboard 62. The images are constructed for presentation on the console using known construction algorithms which are performed by a general purpose computer such as a RISC system/6000 computer system available from the IBM Corporation. This computer system is typically housed in a separate housing and connected to the console 60 by appropriate cabling.

Figure 2:
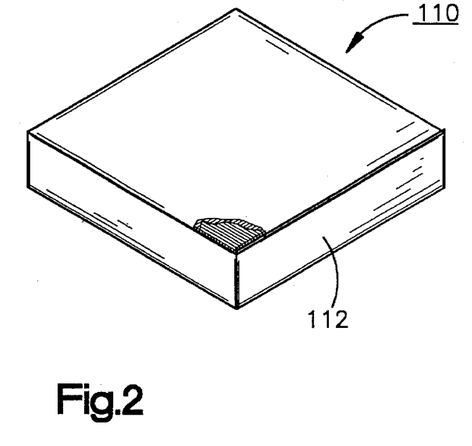
FIG. 2 is a perspective view of a detector for monitoring penetrating radiation from a subject.
Figure 3:
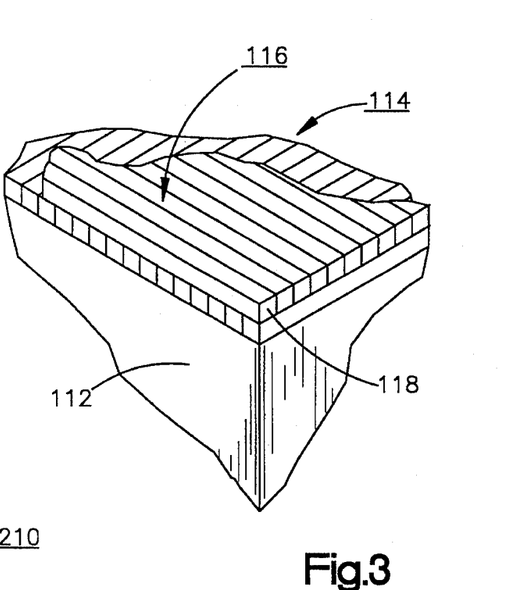
FIG. 3 is an enlarged, fragmentary perspective view of the FIG. 2 detector.

A detector 110 depicted in FIGS. 2 and 3 consists of an energy resolving scintillating material 112 and two orthogonally arranged arrays of spatially resolving, parallel scintillating fibres 114, 116. The scintillator 112 is a prismatic rectangular solid composed of a scintillating material such as thallium-activated sodium iodide. The arrays of scintillating fibres 114, 116 are supported on a planar surface shown in FIGS. 2 and 3 above the surface of the scintillating material 112. Each fibre (such as fibre 118 in FIG. 3) is composed of a scintillating material such as styrene doped with butyl-PBD and POPOP. The fibres in the array 114 are perpendicular to the fibres in the array 116 so that the fibres in the array 116 provide resolution along one dimension (e.g., the x-direction in FIG. 2) while the array 114 provides resolution in a perpendicular direction along the surface of the detector 110 (e.g., the y-direction in FIG. 2). The arrays 114, 116 and the crystal 112 are adjacent so that gamma radiation may pass from the arrays 114, 116 to the crystal 112.

An array of photodiodes or photomultiplier tubes ["PM tubes"] (not shown) is positioned along one side of the fibre array 116, with one of the photodiodes or PM tubes aligned with and optically coupled to an end of each fibre (or a small group of such fibres) in the array 116 to detect light conducted by that fibre. Similarly, a second array of photodiodes or PM tubes is positioned along one side of the fibre array 114 along a direction perpendicular to that of the first array of photodetectors, with one of the photodiodes or PM tubes aligned with and optically coupled to an end of each fibre in the array 114 to detect light conducted by that fibre. Opposite ends of the fibres in the arrays 114, 116 are silvered to minimize light loss. Light energy within a fibre of either array 114, 116 is retained in that fibre by reflection off the boundaries or the silvered ends of the fibre, and conducted toward the photodetector aligned with the end of that fibre. Alternatively, the entire fibre may be silvered except for the photodetector end, so that substantially all of the light generated will be detected.

The arrays 114, 116 define an x-y coordinate grid which serves to determine the position of a photon of gamma radiation exiting the patient and impinging on the detector 110. Such radiation first impinges on the array 116. A photon of gamma radiation striking a fibre in the array 116 and undergoing a Compton event surrenders a portion of its energy as light. This light is conducted by that fibre toward its corresponding photodetector, which generates a coordinate signal when light is detected. This signal is amplified and conducted to the general purpose computer, which relates the fibre in the array 116 with an x-coordinate for the photon of gamma radiation.

A photon of gamma radiation proceeding from the array 116 into the array 114 and undergoing a Compton event in one of the fibres of the array 114 will again surrender a portion of its energy as light. As in the case of fibres in the array 116, this light is conducted by that fibre toward its corresponding photodetector, which generates a signal when light is detected. This signal is amplified and conducted to the general purpose computer, which relates the fibre in the array 114 with an y-coordinate for the photon of gamma radiation. Between the signals generated from the array 116 and the array 114, x-y coordinates for the photon of gamma radiation can be determined.

While only a single layer of x-fibres 116 and a single layer of y-fibres 114 are shown in FIG. 3, additional stacked layers of x- and y-fibres may be included in order to increase the likelihood of Compton events in the fibres.

The scintillating material 112 is preferably much thicker, or has a much larger absorption cross-section, than the fibres of the arrays 114, 116 to provide an additional volume of scintillating material to complete the conversion of gamma radiation into light. A preferred thickness for a scintillating material 112 composed of sodium iodide crystal is on the order of 5 centimeters. One or more photodetectors are positioned and optically coupled to measure the total energy of gamma radiation converted to light in the crystal 112. Surfaces of the crystal other than where it is optically coupled to the photodetectors are preferably silvered to maximize light output to the photodetectors.

The photodetectors generate signals having magnitudes directly related to the intensity of light received from each scintillator 112, 114, 116. These signals are conducted to the general purpose computer in the viewing console 60. Through a coincidence-matching technique, the total energy of light detected from the scintillators 112, 114, 116 within a pre-set time period is correlated with the determined x-y coordinates in the data set from which the image is to be generated. Correlated data sets with total energy readings inside an acceptable energy bandwidth are photopeak signals which are representative of photons of gamma radiation from the radioisotope in the patient of interest and utilized in generating images.

By separating the functions of determining x- and y-coordinates from the measurement of total energy, it is anticipated that the spatial resolution of the detector will be improved by as much as a factor of ten in comparison with prior art detectors. Since the fibres of the arrays 114, 116 are significantly thinner than the 9 millimeter prior art scintillation crystals, the x- and y- resolution is improved. Meanwhile, the increased absorption cross-section of the energy scintillation material 112 relative to the prior art scintillation crystals increases the efficiency by which gamma radiation is converted to light and thereby improves the accuracy of the image for a radiation source of a given strength. Indeed, it is anticipated that approximately 85% of the energy of gamma radiation at 500 keV will be converted to light in the scintillating material 112. In addition, the increased absorption cross-section scintillating material results in better energy resolution (8% as opposed to 11%–12%) and is likely to be more durable and less expensive per pound than the prior art detector crystals.

Figure 4:
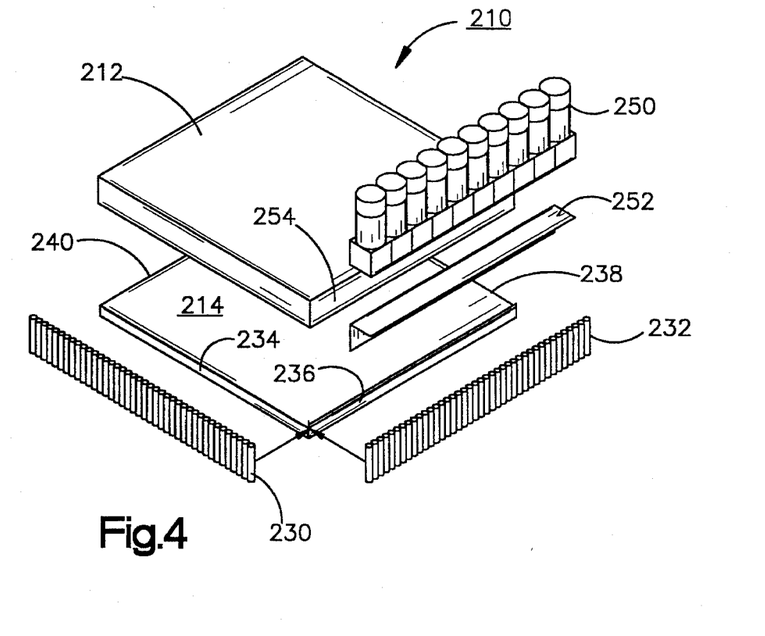
FIG. 4 is a perspective view of an alternative detector for monitoring penetrating radiation from a subject.

An alternative detector 210 is shown in FIG. 4. Like the detector 110 of FIG. 2, the alternative detector 210 of FIG. 4 includes a relatively high absorption cross-section, energy resolving scintillator 212 and an adjacent, relatively low absorption cross-section, spatially resolving scintillator 214. Unlike the arrays 114, 116 of the detector 110, the spatially resolving scintillator 214 of the detector 210 consists of a continuous flat sheet of scintillation material. Arrays of photodetectors 230, 232 are provided along orthogonal sides 234, 236 of the scintillator 214, while opposite sides 238, 240 are silvered to reduce light loss. Alternatively, photodetectors may be placed on all sides of the scintillator 214.

A photon of gamma radiation impinging on the scintillator 214 and undergoing a Compton event surrenders a portion of its light. This light spreads in all directions through the scintillator 214, and is conducted to the detectors 230, 232. The detectors 230, 232 detect the light as distributions of intensity along x- and y- coordinates along the sides 234, 236 of the scintillator 214. The x- and y- coordinates are determined from the centers of the distributions, while the total energy of the light in the scintillator 214 is determined from an integration of the two distributions.

As was true of the scintillation crystal 112 of the detector 110, the scintillator 212 is a prismatic rectangular solid which provides an additional volume of scintillation material beyond the spatially resolving scintillator 214. An array of PM tubes 250 are coupled by means of a Porro prism 252 along a side 254 of the scintillator 212, while the remaining sides 256, 258, 260 of the scintillator 212 are silvered to reflect light back toward the prism 252 and photodetectors 250.

The total energies of photons of gamma radiation are determined from signals from the PM tubes 250 and the photodetectors 230, 232, which are conducted to the general purpose computer and summed. The total energy of light detected from the scintillators 212, 214 within a pre-set time period are correlated with the determined x-y coordinates in the same manner as described previously in order to reject undesired signals from the photodetectors.

Figure 5:
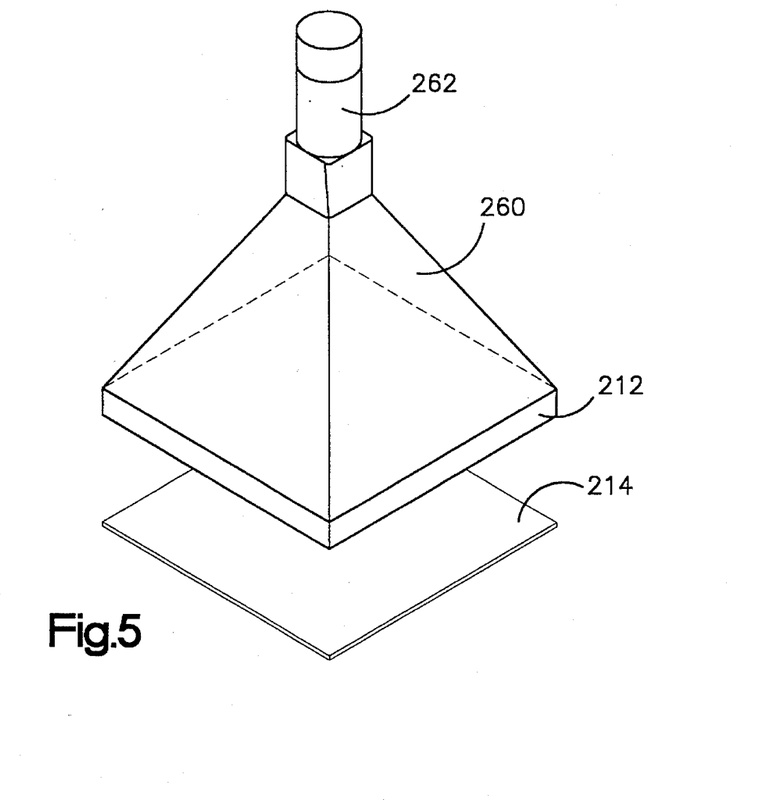
FIG. 5 is conceptual drawing of a method for getting signals from the energy detector.

FIG. 5 is a perspective view of an alternate embodiment of an arrangement for converting outputs from the detector 212 into signals for evaluation by the computer. In this alternate embodiment a glass or plastic focusing member 260 focuses light from the crystal 212 to a single photomultiplier tube 262. In this embodiment, the single photomultiplier tube 262 replaces the array 250 of such tubes shown in FIG. 4. Such an arrangement could also be used in the FIG. 2 detector to sense signals output from the crystal 112.

Figure 6:
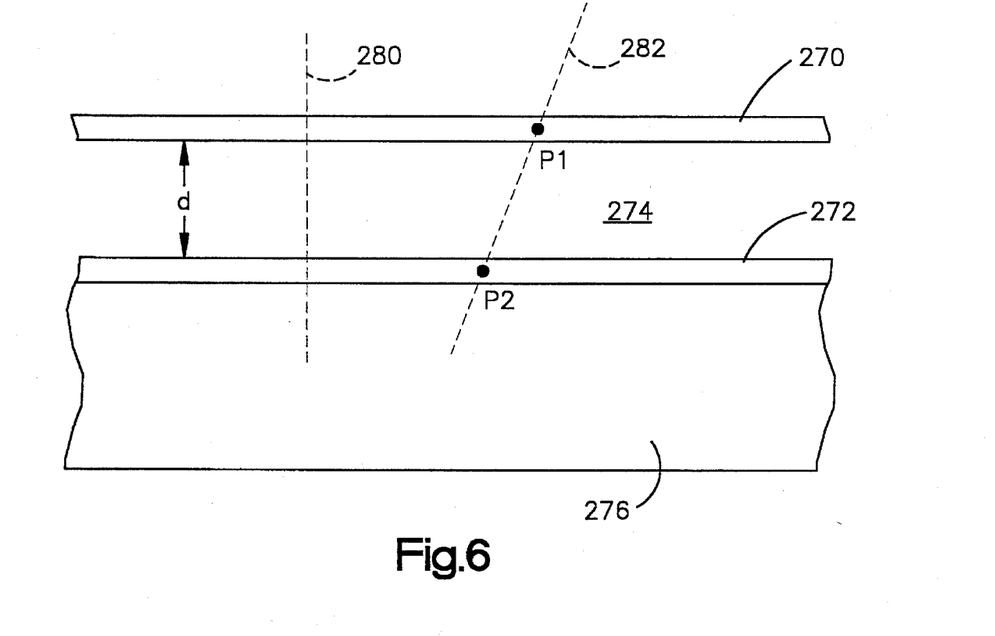
FIG. 6 is conceptual drawing of an alternative method of operating a gamma camera.

Turning now to FIG. 6, this figure shows two parallel position detectors 270, 272 spaced apart by an air gap 274 having a width d. In this arrangement, the second detector 272 is a backed by a thick energy resolving crystal 276. As gamma energy follow different paths 280, 282, it passes through the detectors 270, 272 and impinges upon the energy detector 276. The XY detectors 270, 272 are coupled to appropriate detectors for monitoring signal outputs generated by gamma ray interaction with the detectors 270, 272. As noted above, two points uniquely determine a line and by determining the location of the two points P1, P2, for example, the orientation of the gamma radiation entering the detector can be uniquely determined. This structure avoids the necessity of a separate collimator in a an orbiting detector which, by its design, must monitor radiation entering the detector that is traveling along nonparallel paths.

Figure 7:
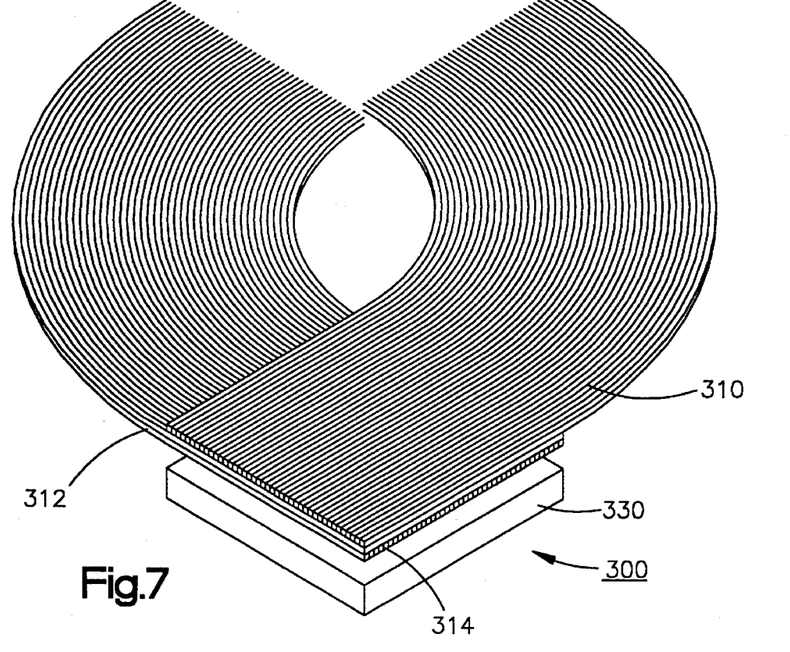
FIG. 7 is a perspective view of an alternate design of a gamma camera detector having a Europium doped Calcium Fluoride layer.

FIG. 7 shows a detector 300 having two wave shifting fiber optics layers 310, 312 that form an x-y or position resolving portion of a gamma camera. Sandwiched between the two layers 310, 312 is a generally square shaped layer of Europium doped Calcium Fluoride ($CaF_2(Eu)$) 314. $CaF_2(Eu)$ was chosen because it has a large Compton cross section in relation to its photoelectric cross section. This means that, relative to Thallium doped Sodium Iodide (NaI(Tl)), which is the typical scintillator typically used in gamma cameras, there is a much higher probability of a given gamma photon having a Compton interaction with the $CaF_2(Eu)$ than with the NaI(Tl). The resultant Compton electron will be absorbed in the $CaF_2(Eu)$ and produce a number of photons, depending on the energy of the Compton electron. These photons will be emitted isotropically.

Some photons will enter each of the two fiber optic layers 310, 312 and will be shifted by the wave shifting fiber optics on each side of the $CaF_2(Eu)$ layer. These wave shifting fiber optics are readily available in the market. The wavelength shifted light will be detected by a multianode photomultiplier tube, also readily available in the market. At the region of the Calcium Fluoride layer 314, individual fibers are aligned parallel to each other and generally perpendicular to fibers in the other fiber optic layer. Because of internal reflection, only those fibers close to the Compton event will capture and shift photons. By analyzing the fibers that provide outputs coincident with each other, analyzing circuitry can determine the spatial or XY location where the Compton event occurred with high accuracy.

Figure 8:
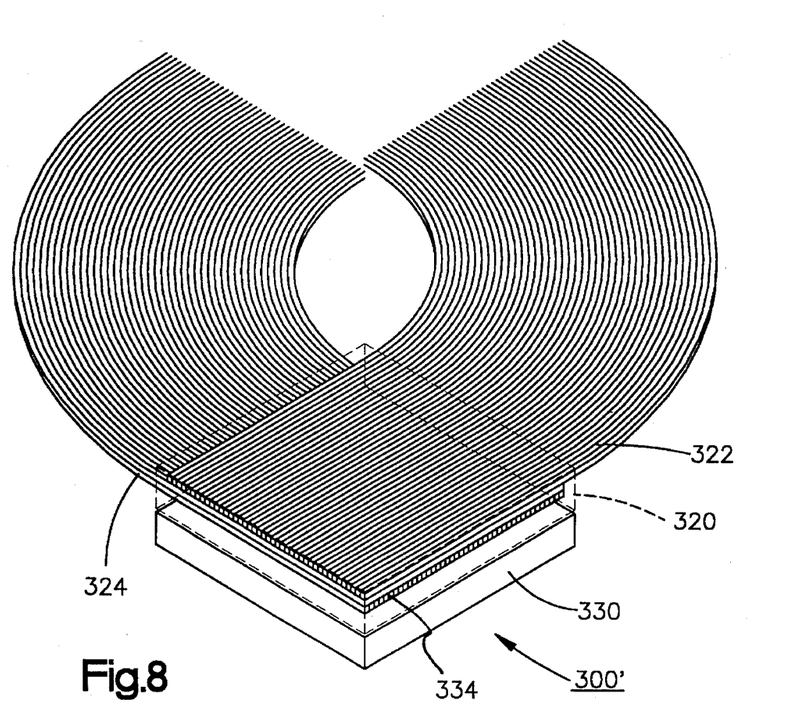
FIG. 8 is a perspective view of a second detector having a Europium doped Calcium Fluoride layer.

The detector 300' as shown in FIG. 8 will operate in much the same manner as that in FIG. 7. In FIG. 8, there may be a better light injection into the wave shifting fibers because they are essentially buried in a $CaF_2(Eu)$ slurry/casting 320. The casting 320 is made by grinding $CaF_2(Eu)$ into a fine powder and mixing it with epoxy. The fibers are laid out in two orthogonal layers 322, 324 and then the slurry/epoxy mixture is cast around them.

After the gamma photon has a Compton interaction with the $CaF_2(Eu)$ in either FIG. 7 or 8, the initial gamma photon has a high probability of being scattered at a relatively low angle. Because a large, energy detecting NaI(Tl) crystal 330 is in close proximity to the XY spatial detector, this photon will most likely be absorbed in the layer 330 and allow a resultant energy of the initial photon to be determined by a "Z" analyzing circuit.

While the drawings show a limited view of the XY spatial detector, there is no physical or manufacturing reason why they cannot be made to fit any size or shape detector configuration. A gap between the spatial and energy detection sections of the detector assembly is most preferably used to position a thin opaque sheet of material 334 that is opaque to light transmission to prevent any backscatter of light from the energy crystal 330 into the wave shifting fibers.

Many modifications and variations of the invention will be apparent to those skilled in the art in light of the foregoing detailed disclosure. Therefore, it is to be understood that, within the scope of the appended claims, the invention may be practiced otherwise than as specifically shown and described.

We claim:

1. A diagnostic imaging gamma camera for developing an image of a spacial distribution of penetrating radiation emanating from a body comprising:
   a) a pair of superposed, Compton event producing layers;
   b) each of the layers including a set of elongate light conductors of relatively small transverse dimension each extending from a region wherein Compton event will occur to an output;
   c) the light conductors of one of the layers being arranged in transverse relationship to the light conductors of the other layer whereby to provide x and y coordinant light signals when a given ray causes Compton events in both layers;
   d) x and y coordinant detectors respectively optically coupled to the light conductors of the one and of the other of the layers;
   e) the layers having input and output sides;
   f) a photopeak producing element superposed with the layers on the output side of the layers for converting to light energy the remaining energy of an electromagnetic ray that has produced Compton events in both layers; and
   g) a photopeak signal detector optically coupled to the photopeak producing element for producing outputs which may be summed with substantially coincident outputs from the x and y coordinate detectors to produce z energy signals.

2. The camera of claim 1 wherein the light conductors are parallel strands.

3. The camera of claim 1 wherein the layers are generally planar.

4. The camera of claim 1 wherein the light conductors of the one layer are orthogonal to the other layer.

5. The camera of claim 1 wherein at least some of the light conductors are phosphorous which emit light in response to Compton events.

6. The camera of claim 1 wherein there is a collinator on the input side of the layers.

7. A diagnostic imaging gamma camera for developing an image of a spacial distribution of penetrating radiation emanating from a body comprising:
   a) a pair of superposed, generally planar, Compton event producing layers;
   b) each of the layers including a set of parallel light conductors of relatively small transverse dimension each extending from a region wherein Compton events will occur to an output;
   c) the light conductors of one of the layers being arranged in orthogonal relationship to the light conductors of the other layer whereby to provide x and y coordinant light signals when a given ray causes Compton events in both layers;
   d) x and y coordinant detector respectively optically coupled to the light conductors of the one of the other of the layers;
   e) the layers having input and output sides;
   f) a photopeak producing element superposed with the layers on the output side of the layers for converting to light energy the remaining energy of an electromagnetic ray that has produced Compton events in both layers; and
   g) a photopeak signal detector optically coupled to the element for producing outputs which may be summed with substantially coincident outputs from the coordinate detectors to produce z signals.

8. The camera of claim 7 wherein at least some of the light conductors are phosphorous which emit light in response to Compton events.

9. The camera of claim 7 wherein the light conductors are parallel strands.

10. The camera of claim 7 wherein there is a collinator on the input side of the layers.

11. A method of producing a diagnostic image of a portion of a patient to whom a radioactive isotope has been administered, the method comprising:
    a) collimating radiation emanating from the patient;
    b) positioning a three scintillation layer detector to receive collimated radiation with the first two layers in the direction of travel of collimated radiation being Compton event layers and the third being a photopeak event layer;
    c) producing x and y coordinate signals in response to Compton events in the first two layers;
    d) summing each set of substantially coincident events occurring in each of the layers in response to a given ray to produce in each case an energy signal;
    e) analyzing each energy signal to determine if its three summed events represent a photopeak event; and,
    f) developing an image comprised of coordinate located spots each representative of a summed energy signal representative of a photopeak event.

12. A diagnostic imaging gamma camera for developing an image of a spacial distribution of penetrating radiation emanating from a body comprising:
    a) two pairs of superposed, generally planar, Compton event producing layers;

b) each of the layers including a set of parallel light conductors of relatively small transverse dimension each extending from a region wherein Compton events will occur to an output;

c) the light conductors of each pair being parallel and the conductors of one of the pairs being arranged in orthogonal relationship to the light conductors of the other pairs whereby to provide two x and two y coordinant light signals when a given ray causes Compton events in both layers;

d) x and y coordinant detectors respectively optically coupled to the light conductors of the one pair and of the other pair of the layers;

e) the layers having input and output sides;

f) a photopeak producing element superposed with the layers on the output side of the layers for converting to light energy the remaining energy of an electromagnetic ray that has produced Compton events in both layers; and g) a photopeak signal detector optically coupled to the element for producing outputs which may be summed with substantially coincident outputs from the coordinate detectors to produce z signals.

13. A diagnostic imaging gamma camera for developing an image of spacial distribution of penetrating radiation emanating from a body comprising:

a) coordinate signal producing means for producing spacial locating output signals in response to gamma ray produced Compton events;

b) the signal producing means having ray input and output sides;

c) a photopeak producing element superposed with the signal means on the output side of the signal means for converting to light energy the remaining energy of an electromagnetic ray that has produced coordinate signals resulting from at least one Compton event in the signal means; and d) a photopeak signal means optically coupled to the photopeak producing element for producing outputs in response to ray induced energy emitted by the element to produce a z energy signal resulting in image producing data each time such emitted ray induced energy is of predetermined value.

14. The camera of claim 13 wherein the signal means includes light conductors which are parallel strands.

15. The camera of claim 14 wherein the strands are generally in planar layers.

16. The camera of claim 15 wherein the light conductor strands of the one layer are orthogonal to the other layer.

17. The camera of claim 14 wherein at least some of the light conductors are phosphorous strands which emit light in response to Compton events.

18. The camera of claim 13 wherein there is a collimator on the input side of the signal means.

19. The camera of claim 13 wherein said signal means sums element outputs with substantially coincident spacial output signals to produce said z energy signals.

20. A method of producing a diagnostic image of a portion of a patient to whom a radioactive isotope has been administered, the method comprising:

a) positioning a scintillation detector to receive radiation from a subject;

b) producing x and y coordinate signals in response to Compton events in a coordinate signal producing means;

c) producing energy signals with a photopeak producing element in response to rays emitted from the signal means;

d) analyzing each energy signal to determine if it represents a photopeak event; and e) developing an image comprised of coordinate located spots each in response to an energy signal representative of a photopeak event.

21. The process of claim 20 wherein the step of analyzing each energy signal includes summing the coordinate signals resulting from a given incident ray with the signal produced by the element in response to said given ray.

22. The process of claim 20 including the step of collimating radiation emitted by the subject.

23. The process of claim 22 including performing the coordinate signal producing step by utilizing two layers of orthogonally disposed parallel light conductors to produce the coordinate signals.

24. A method of producing a diagnostic image of a portion of a patient to whom a radioactive isotope has been administered, the method comprising:

a) positioning a three scintillation layer detector to receive collimated radiation with the first two layers in the direction of travel of collimated radiation being Compton event layers and the third being a photopeak event layer;

b) producing x and y coordinate signals in response to Compton events caused by a given gamma ray in the first two layers;

c) producing an energy signal in the photo peak event layer in response to said given ray;

d) analyzing said energy signal produced to determine if it represents a photopeak event;

e) repeating steps (b), (c) and (d) for each of a series of given events; and, f) developing an image comprised of coordinate located spots each representative of a summed energy signal representative of a photopeak event.

25. The method of claim 24 wherein the step of analyzing each energy signal includes summing the coordinate signals resulting from each such given incident ray with the signal produced by the photopeak event layer in response to the same said given ray.

26. The method of claim 24 including the step of collimating radiation emitted by the patient.

27. The method of claim 24 including performing the coordinate signal producing step by utilizing two layers of orthogonally disposed parallel light conductors to produce the coordinate signals.

28. A diagnostic imaging gamma camera for developing an image of spacial distribution of penetrating radiation emanating from a body comprising:

a) coordinate signal producing members for producing spacial locating output signals in response to gamma ray produced Compton events;

b) the signal producing members having ray input and output sides;

c) a photopeak producing element superposed with the signal members on the output side of the signal means for converting to light energy the remaining energy of an electromagnetic ray that has produced coordinate signals resulting from at least one Compton event in each of the signal members; and d) a photopeak signal mechanism coupled to the photopeak producing energy element for producing outputs in response to ray induced energy emitted by the element to produce a z energy signal resulting in image producing data each time such emitted ray induced energy is of predetermined value.

29. The camera of claim 28 wherein the signal members include light conductors which are parallel strands.

30. The camera of claim 29 wherein the strands are generally in planar layers.

31. The camera of claim 30 wherein the light conductor strands of the one layer are orthogonal to the other layer.

32. The camera of claim 29 wherein at least some of the light conductors are phosphorous strands which emit light in response to Compton events.

33. The camera of claim 28 wherein there is a collimator on the input side of the signal members.

34. The camera of claim 28 wherein said signal mechanism sums energy outputs with substantially coincident spacial output signals to produce said z energy signals.

* * * * *